United States Patent [19]

Jouvin

[11] Patent Number: 4,484,890
[45] Date of Patent: Nov. 27, 1984

[54] IMPRESSION TRAY FOR DENTAL PROSTHESES

[76] Inventor: Jean-Luc Jouvin, 42 Ave. du General Leclerc, 72000 Le Mans, France

[21] Appl. No.: 477,614

[22] Filed: Mar. 22, 1983

[30] Foreign Application Priority Data

Apr. 6, 1982 [FR] France .............................. 82 05917

[51] Int. Cl.³ .............................................. A61C 9/00
[52] U.S. Cl. ........................................ 433/47; 433/37
[58] Field of Search ....................... 433/47, 37, 41, 44, 433/45, 46

[56] References Cited

U.S. PATENT DOCUMENTS

| 980,411 | 1/1911 | Gantz | 433/47 |
| 1,402,298 | 1/1922 | Kidder | 433/46 |
| 1,422,488 | 7/1922 | Smith | 433/46 |
| 1,489,192 | 4/1924 | Cleveland . | |
| 1,499,482 | 7/1924 | Simmons | 433/47 |
| 1,608,632 | 11/1926 | Strusser | 433/47 |
| 2,117,846 | 5/1938 | Kalvin | 433/47 |
| 2,352,545 | 6/1944 | Jefferies | 433/47 |
| 3,978,585 | 9/1976 | Holcomb | 433/45 |

FOREIGN PATENT DOCUMENTS 967376 11/1950 France .................... 433/43

Primary Examiner—John J. Wilson
Attorney, Agent, or Firm—David B. Harrison

[57] ABSTRACT

An impression tray of rigid massive material is disclosed. The tray forms a generally U-shaped channel for impression paste, and it is split along the smooth bottom of the channel into two releasably connectible sections. Paste retention grooves are formed in the sidewalls of the channel, and these grooves are undercut to retain the paste in the channel when the tray sections are connected. A screw assembly facilitates release of the sections and consequent release and nondestructive removal of the cured dental paste impression. A handle is also formed as an integral extension of the outer section of the tray.

9 Claims, 3 Drawing Figures

IMPRESSION TRAY FOR DENTAL PROSTHESES

BACKGROUND OF THE INVENTION

The present invention relates to an impression tray for dental prostheses, comprising a channel, to take the impression paste, curved in a U shape with diverging arms in a plane roughly parallel to the bottom of the channel, this channel being provided with paste retention means and being prolonged, on the opposite side from its two ends, by a handle to hold it with.

These impression trays are used to take an impression of the teeth in a jaw, from which impression the prosthetist makes a plaster model.

So far impression trays have been made in pressed sheet metal, with the paste being retained in the channel by means of holes perforated in it.

There are many drawbacks to these known impression trays.

Although the impression trays are made of deformable thin sheet metal difficulties arise in stripping the plaster model from the impression and in subsequently removing the impression from the impression tray. In general the impression is damaged or even destroyed. It is therefore not possible to re-use the impression.

Because the impression trays must be deformable in order to allow for stripping they are not rigid enough for application of the so-called "wash technic" method of taking the impressions in two stages, which involves using more rigid silicone-based paste.

Furthermore it is awkward to clean the impression tray since the paste adheres to the retention perforations.

There also exist impression trays, also made of pressed steel, in which paste retention is assured by means of metal wires welded to the top inside edges of the channel. Here again, it is necessary to deform the impression tray to strip the mold. In addition the paste risks being detached from the bottom of the channel, because there is no retention means at that position, when the impression is separated from the jaw (withdrawal). In addition, the fact that there are metal wires on the inside top edges of the channel makes it necessary to make the channel itself very wide, so leading to the use of a large amount of paste.

SUMMARY OF THE INVENTION

The object of this invention is an impression tray for dental prostheses of the type defined above which, whilst providing perfect retention of the paste in the impression tray, enables the mold to be stripped from the model very easily and the impression to be removed from the impression tray without difficulty and without risking damaging the impression, so making it possible to re-use the impression and even preserve it, since this impression tray can be used without difficulty in all impression-taking methods (also two-stage ones) and requires a minimum amount of paste.

The impression tray according to the invention for dental prostheses comprises a channel, to take the impression paste, which is curved in a U shape in a plane roughly parallel to the bottom of the channel. The channel is provided with paste retention means and is prolonged, on the side opposite its two ends, by a handle for gripping it. The impression tray as a whole is made in a rigid massive material. The paste retention means consist of one or more grooves roughly parallel to the bottom of the channel, undercut with respect to the open side of the channel. The channel is divided into two parts, along the bottom, throughout its length, so that the retention grooves have draft in the direction of separation of the two parts, i.e. the direction in which the channel is opened up. The impression tray also comprises assembly means to separably join the two parts of the channel together so that the channel can be split into two parts.

This facility for opening up the channel means, although the channel is made of a rigid material and is therefore not deformable, that the impression can be removed without difficulty, with the plastic model, from the impression tray without damaging the impression in any way, and the plaster model stripped from the impression, since this is no longer retained in the impression tray, and the undamaged impression can be re-used, if need be, since the impression tray can be reclosed over the impression to give it its initial shape.

Preferably, the channel retention grooves comprise, in the channel bottom, a groove having a dovetail profile or a similar undercut profile, the channel being split at the bottom of the said groove. Thus, although the channel bottom retention groove has an undercut cross-section there is no difficulty in stripping the impression from this groove after the channel has been opened.

To provide in addition for retention of the impression on the channel sides the channel has, in each side, at least one groove which, while being undercut with respect to the open side of the channel, has a draft opening towards the groove of the other side in a plane parallel to the channel bottom. When the two channel components are split apart the impression is thus released from these grooves without any problems.

In order to facilitate separation of the two parts of the channel, and above all to facilitate reassembly of the two parts of the channel, it is advantageous for this to comprise means on both parts, engaging with each other during assembly and separation of the two parts, in order to provide mutual guidance of the two parts.

These means may advantageously consist of complementary profiles on the contact surface of the two parts.

Preferably, these complementary guide profiles may comprise, on the contact surface of the two parts, a groove recessed into one of the two parts and a tongue projecting from the other part.

The means of joining the two parts of the channel may be very varied in type. For example it is possible to provide for latch, toggle, etc. systems. However, according to an advantageous embodiment the said assembly means comprise a screw system the center line of which coincides with the axis of symmetry of the channel U.

In order to further facilitate operation of the screw system, and in particular to ease the channel opening operation, it is advantageous for the screw system to comprise a screw, the head of which is captive in a transverse opening in the handle fixed to the outer part of the channel and the shank of which runs freely through the said outer part of the channel, and which is screwed into a tapped hole in the inside part of the channel. This arrangement means that it suffices to turn the screw in the unscrewing direction to perform not only disassembly but also simultaneous forced separation of the two channel parts from each other as soon as the screw head butts against the wall of the opening on the side opposite to the channel itself.

BRIEF DESCRIPTION OF THE DRAWINGS

With reference to the appended drawings we shall describe in greater detail below an illustrative and non-restrictive embodiment of the impression tray according to the invention; In the drawings.

DETAILED DESCRIPTION OF A PREFERRED EMBODIMENT

The impression tray for dental prostheses illustrated by the drawings comprises a part 1 forming a channel designed to take the impression paste, which is not shown. The channel 1 is incurvated, in a plane roughly parallel to the bottom of the channel 1, to form a U with diverging arms, the shape of which corresponds to the line along which the teeth are implanted in the jaws.

Part 1 forming the channel is prolonged, on the side opposite to the channel's open ends, by a gripping handle 2.

Figure 3:
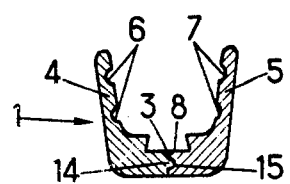
FIG. 3 is a section view of the channel along III—III in FIG. 1.

The channel 1 has a transverse cross-section shaped like a U with diverging sides, as shown in FIG. 3. The channel 1 is split along the smooth bottom surface, throughout its length, along a line marked 3 in FIG. 1, into an inner section 4 and an outer section 5. The outer section is made in one piece with the handle 2.

Each side of the channel 1, i.e. each of the two sections 4 and 5 of the channel, comprises on the inside two grooves 6, 7 placed one above the other and running over the whole length of the channel 1. Grooves 6 and 7 are undercut or have negative draft with respect to the upper opening of the channel 1.

In addition the channel 1 has, in the bottom, a dovetail groove 8, i.e. one which is also undercut with respect to the upper opening of the channel 1. The line 3 dividing the channel 1 into two sections 4 and 5 runs along the bottom of the groove 8.

The two sections 4 and 5 of the channel 1 are joined by means of a screw 9 whose center line coincides with the axis of symmetry of the channel 1 U-shape. The head 10 of the screw 9 is captive in a transverse opening 11 in the handle 2. The shank 12 of the screw 9 passes freely through the outer section 5 of the channel 1 and is screwed into the inner section 4, which comprises a tapped hole, not shown, for this purpose.

Figure 1:
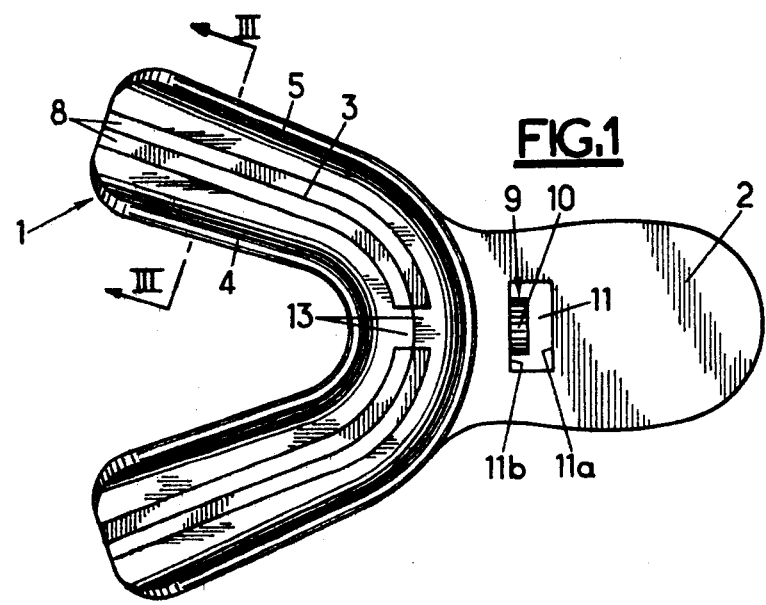
FIG. 1 is a plan view of an impression tray according to the invention, with the channel closed.
Figure 2:
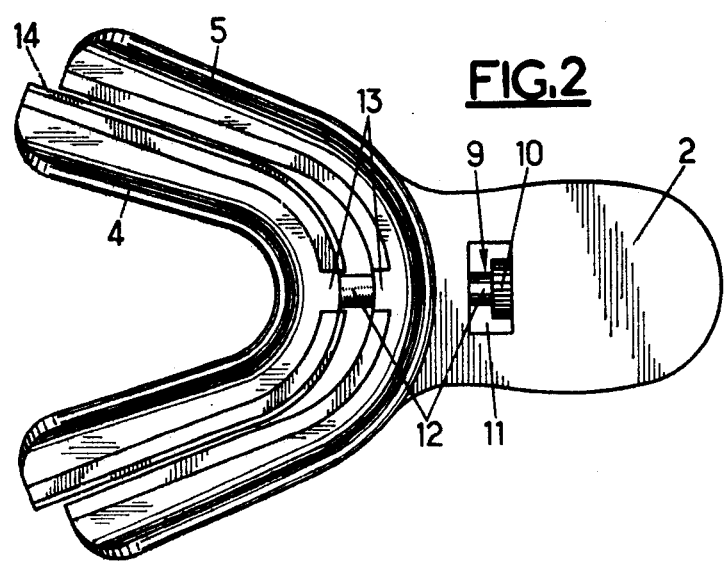
FIG. 2 is a plan view of the impression tray in FIG. 1, with the channel partly opened.

It can be seen in FIGS. 1 and 2 that the trapezoidal groove 8 located in the bottom of the channel 1 is broken in the middle of the length of the channel 1 at 13. This part 13 acts as a stop, when taking the impression, to limit the sinking of the incisors into the paste, not shown, contained in the channel 1.

When taking an impression the impression paste is placed in the channel 1 in the closed position shown in FIG. 1. The impression is taken in the usual way, with the channel being presented with its open side facing the dentition whose impression has to be taken; the dentist applies pressure on the impression tray so that the patient whose impression is being taken is driven into the paste. The impression can be taken either in one stage or also in two stages with intermediate removal, as is the known case with hard silicone-base impression pastes (Wash Technic).

The grooves 6, 7 and 8, which are all undercut with respect to the open side of the channel 1, provide perfect retention of the paste during removal of the impression from the teeth. After this removal the dentist removes the surplus paste from along the edges of the impression tray by means of a scalpel blade, for example, since the surplus paste which has run outside the channel and been pressed back by the lips or tongue onto the outside faces of the channel is liable to prevent the demountable impression tray from opening.

The dental technician, who receives the impression held in the impression tray, carries out the casting of a plaster mode of the impression. In order then to strip the plaster model from the mould the dental technician turns the screw 9, the head 10 of which is advantageously knurled, in the unscrewing direction. The whole screw then moves rightwards in FIG. 1 until the head 10 bears against the "rear" edge 11a on the right of the opening 11. Since the screw 9 can no longer move rightwards any further unscrewing of the screw 9 leads to forced movement left of the inner section 4 of the channel and therefore to forced opening of the mold formed by the channel 1. The dental technician can continue this unscrewing action until the shank 12 of the screw 9 is completely unscrewed from the tapped hole in the inner section 4 of the channel 1, so that section 4 is released. The dental technician then has no difficulty in removing the impression with the plaster model and stripping the model without damaging the impression which is no longer held captive in the impression tray channel.

In order to subsequently close the impression tray the inner section 4 of the channel only has to be presented in front of the outer section 5 of the channel and the screw 9 operated so as to engage it in the tapped hole in section 4 and then bring sections 4 and 5 together to the position of FIG. 1 where the channel 1 is again closed, the head 10 of the screw 9 being tightened against the "front" edge 11b on the left side of the opening 11.

It should be further noted that, in order to ease closure of the channel 1, the two channel sections 4 and 5 comprise mutual guiding means. In the example shown (FIG. 3), these guide means consist of a tongue 14 projecting from the inner channel section 4 and a groove 15 recessed into channel section 5 on the surface of mutual contact between sections 4 and 5, i.e. below the bottom of the dovetail groove 8.

It would, of course, be possible to replace this tongue and groove system by different means, for example shoulders.

The impression tray according to the invention is made of a massive material, for example of plastics material or of metal, preferably a light alloy. To prevent any risk of the impression paste from adhering to the channel, notably when the impression is fabricated from metal, it may be advantageous to coat at least the channel on the inside with an anti-adhesive material, for example polytetrafluorethylene, or any other fluorinated resin, for example the material sold under the brand name "Fluorimid 10P".

The impression holder as described above and shown in the appended drawings can receive a large number of modifications and variants within the framework of the invention. Thus, the screw system for assembling the two sections of the channel can be replaced by any other assembly system, e.g. catch or toggle systems. The number and profile of the grooves 6, 7 and 8 may also be different. The only important thing is for these grooves to be undercut with respect to the channel opening while, however, permitting stripping of the impression without difficulty after the channel has been opened, i.e. the two sections 4 and 5 of the channel have been separated along the channel axis of symmetry.

An additional advantage of the impression tray according to the invention, due to the possibility of cutting off the surplus paste with a sharp instrument, consists in the certain visual evidence of any distortion, even minute, of the impression paste. It is therefore very easy to assess the dimensional stability of the paste used by observing the clearance which may appear between the edge of the paste and the edge of the impression tray, since the paste is not held by holes and is free to retract. It should be noted that, in practice, all impression pastes retract on aging. The dentist or dental technician can therefore judge the impression quality at the glance and discard those impressions in which aging has caused too large a retraction leading to failures with conventional methods, failures which unfortunately can only be detected on the day the prosthesis is fitted into the patient's mouth.

I claim:

1. An impression tray for dental prostheses comprising a U-shaped structure with divergent arms defining a channel having a U-shaped cross-section with two sidewalls and a bottom, said structure comprising two complementary opposed sections forming sidewall and bottom portions, an outer section and an inner section, said sections being separably connectible along a common mutual contact surface generally normal to and generally following the bottom of said U-shaped channel, said bottom portions containing oppositely undercut grooves along said common mutual contact surface to form a dovetail-like single groove communicating with said channel when said sections are connected together, each section defining at least one undercut groove in its sidewall portion thereof generally parallel to the bottom of said channel for retaining impression paste placed in said channel, said structure further comprising assembly means for connecting the said two sections separably together, so that the two sections may be separated to enable an impression formed by impression past to be removed from, and reinsertable into said tray without being damaged or deformed.

2. The impression tray according to claim 1 wherein said sidewall grooves are formed with generally aligned oppositely facing draft openings.

3. The impression tray according to claim 1 wherein said sections comprise locking alignment means to facilitate and maintain proper alignment of said sections as they become connected together along said mutual contact surface to form said tray.

4. The impression tray according to claim 3 wherein said locking alignment means comprises longitudinally extending complementary interlocking portions disposed on said adjacently opposed faces forming said mutual contact surface.

5. The impression tray according to claim 4 wherein said locking alignment means comprises a groove defined in one of said faces and an aligned corresponding tougue defined on the other of said faces.

6. The impression tray according to claim 1 wherein said assembly means comprises a screw system including a screw whose center line coincides generally with the axis of symmetry of the U-shaped channel.

7. The impression tray according to claim 1 wherein said outer section includes an integrally formed gripping handle extension.

8. The impression tray according to claim 7 wherein said assembly means comprises a screw system including a screw whose center line coincides with the axis of symmetry of the U-shaped channel and having a head held captive within the spatial boundaries of a transverse opening defined in said handle extension, said screw having a shank extending freely through a hole defined in said outer section and further having tapped threads which engage threads of a tapped hole formed in said inner section.

9. The impression tray according to claim 1 further comprising a coating of an impression paste resistant material on the inside surfaces of said tray defining said U-shaped channel, said material for resisting adhesion of said paste to said tray when emplaced and cured in said tray and for facilitating ready removal therefrom after said sections have been disconnected by operation of said assembly means.

* * * * *